United States Patent [19]
Diamond

[11] 3,966,801
[45] June 29, 1976

[54] PHENYL BUTYRIC ACIDS AND DERIVATIVES THEREOF

[75] Inventor: Julius Diamond, Lafayette Hills, Pa.

[73] Assignee: William H. Rorer, Inc., Fort Washington, Pa.

[22] Filed: Dec. 13, 1973

[21] Appl. No.: 424,628

Related U.S. Application Data

[62] Division of Ser. No. 195,825, Nov. 4, 1971, Pat. No. 3,867,434.

[52] U.S. Cl. ............................................. 260/515 A
[51] Int. Cl.² .......................................... C07C 63/52
[58] Field of Search .................................. 260/515 A

[56] References Cited
UNITED STATES PATENTS

| | | |
|---|---|---|
| 2,240,275 | 4/1941 | Whitmore et al. ................... 260/515 |
| 2,679,500 | 5/1954 | Gash et al. ........................... 260/515 |
| 2,798,091 | 7/1957 | Mavity ................................. 260/515 |
| 3,090,808 | 5/1963 | Kharasch et al. ................... 260/515 |
| 3,435,075 | 3/1969 | Glamkowsi et al. ................. 260/515 |
| 3,472,646 | 10/1969 | Euc et al. ............................. 260/515 |

*Primary Examiner*—James A. Patten
*Attorney, Agent, or Firm*—Erich M. H. Radde; Dayton R. Stemple, Jr.

[57] ABSTRACT

Novel substituted phenyl butyric acids and their derivatives are described. Therapeutic compositions and method of treatment of inflammation is also disclosed.

2 Claims, No Drawings

PHENYL BUTYRIC ACIDS AND DERIVATIVES THEREOF

CROSS REFERENCE TO RELATED APPLICATIONS

The present application is a Division of Application Serial No. 195,825 filed November 4, 1971, and entitled "PHENYL BUTYRIC ACIDS AND DERIVATIVES THEREOF", now Patent No. 3,867,434.

SUMMARY OF THE INVENTION

This invention describes novel halo butyric acids and their derivatives and their use in therapeutic compositions. In addition, this invention describes the preparation of these halo butyric acids and their derivatives. When the compounds of this invention are administered to mammals, they afford significant treatment for the relief of inflammation and associated pain and fever.

They further provide analgesic and antipyretic methods for the relief and treatment of pain and fever.

BACKGROUND OF THE INVENTION

Continued studies have been carried out in research to develop drugs which would significantly inhibit the development of inflammation and relieve the pain and fever associated with it. While much of this effort has been carried out in the steroid field these have been compounds developed which are non-steroidal and have included such as the alkanoic acids derived from biphenyl, stilbene, indole, naphthylene and various heteryl rings. While many of these compounds have been found to be effective, they have had the drawback of causing various side effects or being effective only on a specific disorder.

I have unexpectedly found that when halogen is present in the α-position of the side chain of a substituted phenylbutyric acid molecule, pharmacological properties exist in the molecule which are useful for the relief and inhibition of inflammation conditions.

I have also found that the compounds of this invention are effective in the treatment of inflammation and the control of arthritic conditions associated with inflammation.

I have further found that α-halo phenylbutyric acids and their derivatives are novel.

I have also found that the compounds of this invention possess useful analgesic and antipyretic properties and are useful in the treatment of pain and fever.

I have still further found an entirely new class of antiinflammatory, analgesic and antipyretic pharmaceutical compositions which contain an α-halo phenylbutyric acid or derivative thereof as active ingredient.

I have also found a convenient method for synthesizing these compounds.

DESCRIPTION AND PREFERRED EMBODIMENTS

This invention comprises a class of novel chemical compounds which have a phenylbutyric acid group or derivative to which is attached a halo, mercapto, or thio derivative at the α-, β- or γ-position. Also the phenyl ring may further be substituted.

This invention also describes a new method for treating inflammation as well as pain and fever and also novel therapeutic compositions.

The following numbering system is used in this invention:

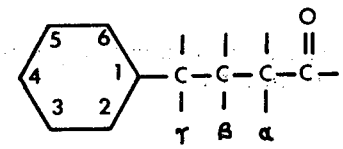

The compounds of this invention can be represented by the generic structure which is described by the general formula I;

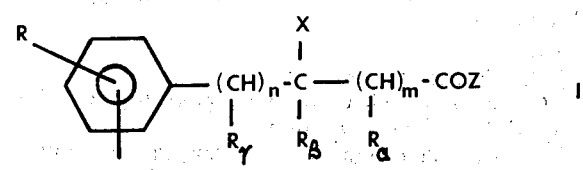

where:
R is
  alkyl,
Y is
  hydrogen,
$n + m = 2$;
$R_\alpha$, $R_\beta$ and $R_\gamma$ are hydrogen;
X is in the α-position and is halo;
Z is
  hydroxyl —OH,
  loweralkoxy,
  arloweralkoxy, or,
  —OM (where M is an alkali, alkaline earth or aluminum metal or an ammonium salt).

The compounds of this invention contain at least one asymmetric carbon atom in the butyric acid side chain. As a result, the above compounds of formula I may be obtained as racemic mixtures of their dextro (+) and levorotatory (—) isomers. It is to be understood that said d and l isomers as well as the dl mixtures thereof are embraced within the scope of this invention.

More specifically, the chemical compounds of this invention which have particular usefulness as antiinflammatory, analgesic and antipyretic agents are described by formula II,

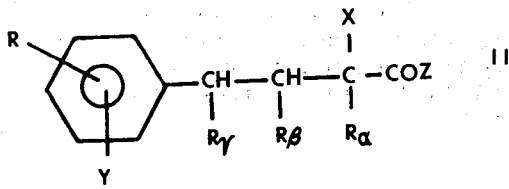

Those compounds whose properties are preferred are described by formula III:

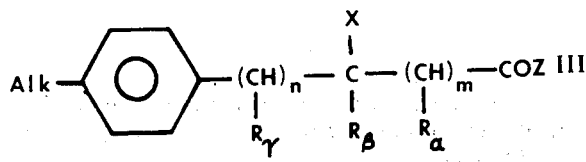

where Alk is alkyl having 3-7 carbon atoms

Those compounds whose properties are even more preferred are described by formula III where Y is hydrogen
and $R_\alpha$, $R_\beta$ and $R_\gamma$ are hydrogen.

Compounds which are most preferred are those where X is in the $\alpha$-position.

A special embodiment of this invention describes a method for inhibiting inflammation and the treatment of pain and fever associated with inflammation as well as having analgesic and antipyretic effectiveness for the relief and treatment of pain and fever not symptomatically related to an inflammation indication. This method affords relief by the administration of a compound of Formula I where
X is
  halo.

In the descriptive portions of this invention the following definitions apply:

"alkyl" refers to a loweralkyl hydrocarbon group containing from 1 to about 7 carbon atoms which may be straight chained or branched.

"alkoxy" refers to a loweralkoxy group containing from 1 to about 6 carbon atoms which may be straight chained or branched.

The preferred "alkali" or "alkaline earth" metals are sodium, potassium, calcium and magnesium.

The term "ammonium salt" refers to the cation formed when ammonia or an organic amine react with the carboxyl group to form ammonium salts of the structure given in the formula. The ammonium salts are formed with a (1) loweralkylamines such as methylamine, diethylamine, triethylamine; (2) hydroxyloweralkylamines such as $\beta$-hydroxyethylamine; (3) heterocyclic amines such as 2-aminopyridine, piperazine, piperidine; (4) aralkylamines such as $\alpha$-methylbenzylamine, phenethylamine; (5) cycloalkylamines such as cyclohexylamine; (6) alkaloids such as quinine, cinchonidine, cinchonine, ephedrine.

Representative compounds of this invention which are particularly useful are as follows:
$\alpha$-chloro-$\gamma$-(o-tolyl)butyric acid
$\alpha$-chloro-$\gamma$-(m-tolyl)butyric acid
$\alpha$-chloro-$\gamma$-(p-tolyl)butyric acid
$\alpha$-chloro-$\gamma$-(p-ethylphenyl)butyric acid
$\alpha$-chloro-$\gamma$-(p-propylphenyl)butyric acid
$\alpha$-chloro-$\gamma$-(p-i-propylphenyl)butyric acid
$\alpha$-chloro-$\gamma$-(p-butylphenyl)butyric acid
$\alpha$-chloro-$\gamma$-(p-i-butylphenyl)butyric acid
$\alpha$-chloro-$\gamma$-(p-sec-butylphenyl)butyric acid
$\alpha$-chloro-$\gamma$-(p-t-butylphenyl)butyric acid
$\alpha$-chloro-$\gamma$-(p-pentylphenyl)butyric acid The $\alpha$-position Claisen condensation of a substituted benzaldehyde with an active acid ester (preferably a loweralkyl or benzyl ester) in the presence of a metal alkoxide results in a $\beta$-acrylic acid ester. The aldehyde may also be subjected to a Perkin reaction with acetic anhydride and an acetic acid salt or through a Knoevenagel condensation using malonic acid and ammonia in an amine base to obtain a substituted $\beta$-acrylic acid. Hydrogenation of the double bond in the presence of a heterogeneous catalyst results in the propionic acid or ester. Conversion of the propionic acid to the acid halide followed by Rosenmund reduction in the presence of a supported catalyst results in the propionaldehyde. This in turn is treated with cyanohydrin to afford the propionaldehyde cyanohydrin which is then hydrolyzed to the $\alpha$-hydroxybutyric acid. The ester or amide may also be prepared in the same manner.

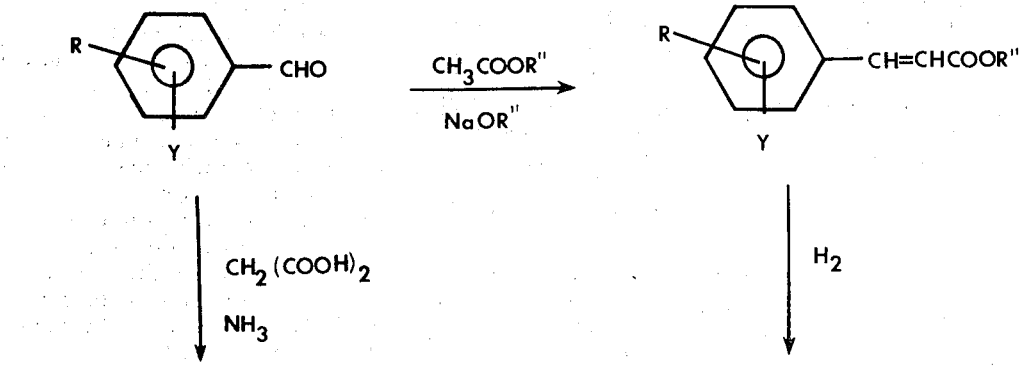

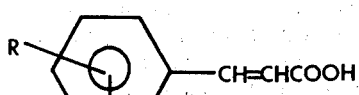
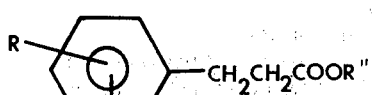
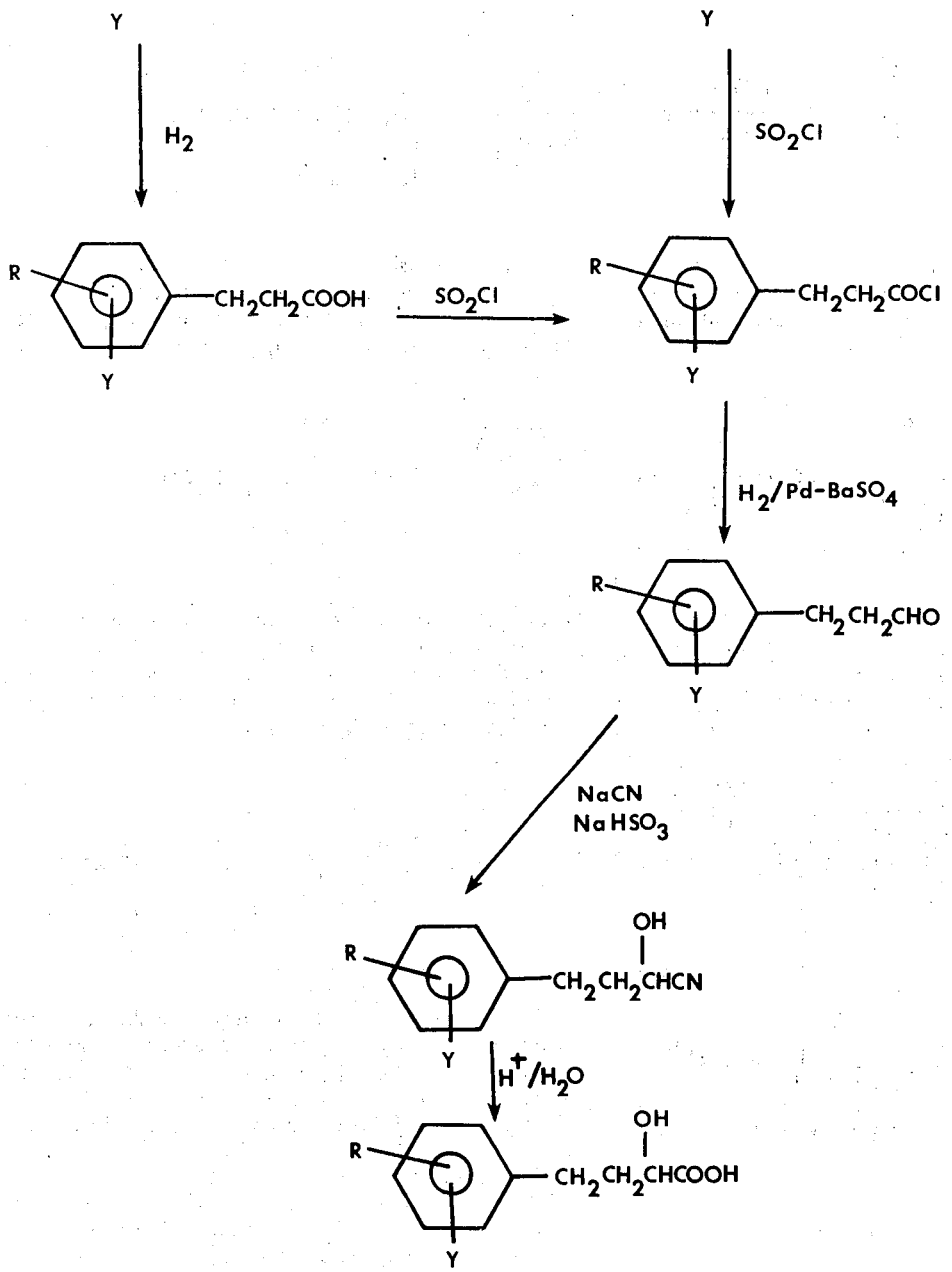
When a substituted hydroxybutyrate is reacted with a phosphorus trihalide, phosphorus pentahalide, phosphorus oxyhalide, sulfurylhalide, thionyl halide, or sulfur halide, the corresponding substituted halo butyrate is prepared.
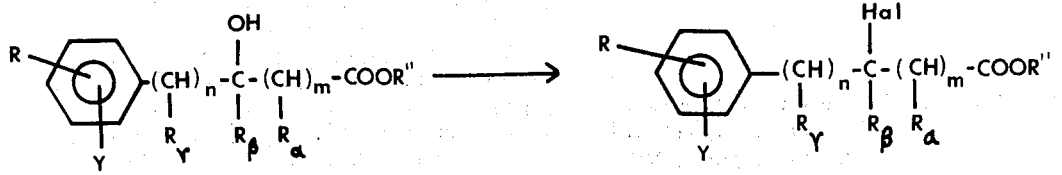

where R'' is lower alkyl;
where Hal is chloro, bromo or iodo.

Reaction of a sulfonate derivative with a metal halide (preferably an alkali halide) results in the corresponding halo compound.

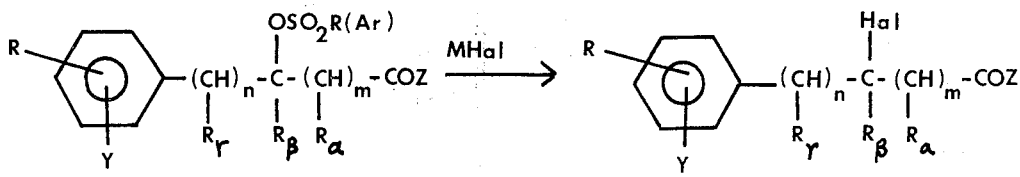

where Z is a described earlier.

The corresponding halo butyric acid may be prepared by heating the ester with acetic acid containing the corresponding hydrogen halide.

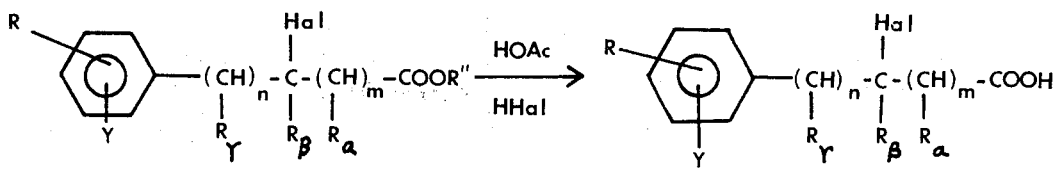

where R'' is lower alkyl.

The substituted fluoro compounds may also be obtained from the corresponding iodo, bromo or chloro compounds by reaction with potassium fluoride at about 130°–200°C.

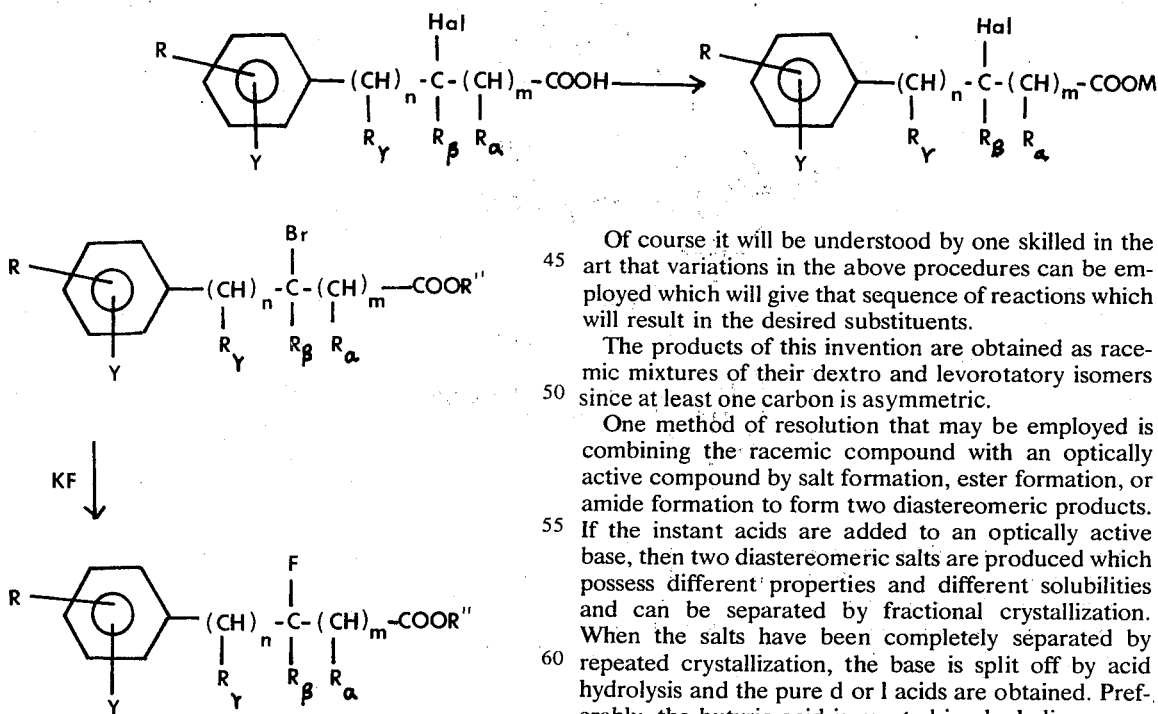

The acid addition salts may be formed by the action of one equivalent of a suitable base with the substituted halo butyric acid. Suitable bases thus include for example the alkali metal alkoxides such as sodium methoxide, etc., and the alkali metal and alkaline earth metal hydroxides, carbonates, bicarbonates, etc. (such as sodium hydroxide, potassium hydroxide, calcium hydroxide, potassium carbonate, sodium bicarbonate, magnesium bicarbonate, etc.). Also, the aluminum salts of the instant products may be obtained by treating the corresponding sodium salt with an appropriate aluminum complex such as aluminum hydroxy chloride hexahydrate, etc. The ammonium salts may be made by reaction with the corresponding amine such as methylamine, diethylamine, β-hydroxyethylamine, piperazine, piperidine, α-methylbenzylamine, cyclohexylamine, triethylamine, phenethylamine, etc.

Of course it will be understood by one skilled in the art that variations in the above procedures can be employed which will give that sequence of reactions which will result in the desired substituents.

The products of this invention are obtained as racemic mixtures of their dextro and levorotatory isomers since at least one carbon is asymmetric.

One method of resolution that may be employed is combining the racemic compound with an optically active compound by salt formation, ester formation, or amide formation to form two diastereomeric products. If the instant acids are added to an optically active base, then two diastereomeric salts are produced which possess different properties and different solubilities and can be separated by fractional crystallization. When the salts have been completely separated by repeated crystallization, the base is split off by acid hydrolysis and the pure d or l acids are obtained. Preferably, the butyric acid is reacted in alcoholic or acetone solution with an equivalent amount of the optically active primary, secondary or tertiary amine such as cinchonidine, cinchonine, quinine, ephedrine, α-methylbenzylamine, sec-butylamine, sec-amylamine, etc. The diastereomeric amine salts produced thereby, are separated by fractional crystallization and each optically active salt is hydrolyzed with dilute mineral acid to produce the dextro or levo form of the butyric acid. Each optical isomer may be reacted then with X'—Cl or XOX' to produce the corresponding optically active alcoholic derivative. Alternatively, an butyrate ester may be reacted with an optically active primary or secondary amine such as ephedrine, α-methylbenzylamine, sec-butylamine, etc., to produce a mixture of diastereomeric butyrates which may be separated by fraction crystallization. Each optically active amide may be hydrolyzed with mineral acid to its respective optically active acid.

Alternatively, a butyrate may be reacted with an optically active alcohol such as 1-menthol or d-borneol, or 1-α-methylbenzylalcohol, to produce a mixture of diastereomeric butyrate esters which may be separated by fractional crystallization. Each optically active ester may be hydrolyzed with mineral acid or alkali to its respective optically active acid. The optically active acids can also be recovered from the α-methylbenzyl esters by hydrogenolysis in the presence of palladium. In this manner the α-halo isomers may be prepared.

I have found that the compounds of this invention exercise a useful degree of anti-inflammatory activity in mammals and are effective in the treatment of associated pain and fever and in like conditions which are responsive to treatment with anti-inflammatory agents. In general, the compounds of this invention are indicated for a wide variety of mammalian conditions where the symptoms of inflammation and associated fever and pain are manifested. Exemplary of such conditions are: rheumatic diseases such as rheumatoid arthritis, osteoarthritis and other degenerative joint diseases; soft-tissue rheumatism such as tendinitis; muscular rheumatism such as sciatica; pain and inflammation associated with dental surgery and similar human and veterinary disease conditions exhibiting the foregoing symptoms requiring the use of an anti-inflammatory, analgesic and/or an antipyretic agent.

For these purposes, the compounds of this invention are normally administered orally, topically, parenterally or rectally. Orally, these may be administered in tablets, capsules, suspensions or syrups; the optimum dosage, of course, depending on the particular compound being used and the type and severity of the condition being treated. In any specific case the appropriate dosage selected will further depend on factors of the patient which may influence response to the drug; for example, general health, age, weight, etc. Although the optimum quantities of the compounds of this invention to be used in such manner will depend on the compound employed and the particular type of disease condition treated, oral dose levels of preferred compounds when administered to a mammal in dosages of 0.5 to 100 milligrams per kilogram of body weight per day are particularly useful. The preferred range is 0.5 to 15 mg/Kg. Comparative dosages may be used in topical, parenteral or rectal administration.

Dosage forms may be prepared according to any method known to the art for the manufacture of pharmaceutical compositions and such compositions may contain one or more agents; for example, sweetening agents, flavoring agents, coloring agents, preserving agents, etc. Further, the active butyric acids or their derivatives may be administered alone or in admixture with antacids such as sodium bicarbonate, magnesium carbonate, magnesium hydroxide, aluminum hydroxide, magnesium silicate, etc., and non-toxic pharmaceutically acceptable excipients. Such excipients may be, for example, inert diluents such as calcium carbonate, lactose, etc., granulating and disintegrating agents; for example, magnesium stearate, talc, etc., binding agents; for example, starch gelatin, etc., suspending agents; for example, methylcellulose, vegetable oil, etc., dispersing agents; for example, lecithin, etc., thickening agents; for example, beeswax, hard paraffin, etc., emulsifying agents; for example, naturally-occurring gums, etc., and non-irritating excipients; for example, cocoa butter and polyethylene glycols.

Various tests in animals can be carried out to show the ability of the butyric acids and derivatives of this invention to exhibit reactions that can be correlated with anti-inflammatory activity in humans. One such test is the Carrageenan paw edema test, which shows the ability of the instant compounds to inhibit edema introduced by injection of an inflammatory agent such as carrageenan into the tissues of the paw of a rat against non-inflamed controls. The carageenan testing method is known to correlate well with anti-inflammatory activity in humans and is a standard test under to determine anti-inflammatory activity. This correlation can be shown by the activities of compounds known to be clinically active including such as aspirin, phenylbutazone, cortisone, hydrocortisone and prednisolone. In view of the results of this test, the butyric acids and derivatives can be considered to be active anti-inflammatory agents.

One method for measuring the pain threshold of the butyric acids and derivatives is the Randall-Selitto test. Analgesic activity is shown by antinocieceptive testing of the inflamed foot of rats and a measurement of their pain response.

EXAMPLE 1

Ethyl α-chloro-γ-(2'-chloro-4-biphenylyl)butyrate

A mixture of 0.747 mole of ethyl α-hydroxy-γ-(2'-chloro-4-biphenylyl) butyrate is stirred with 106.67 g. (0.895 mole) of thionyl chloride at room temperature for 24 hours and then heated to reflux for 6 hours. The cold reaction mixture is poured into 1125 ml. of ice-cold water with stirring. The mixture is extracted with 800 ml. of ether. The ethereal solution is washed with 450 ml. of cold saturated sodium hydrocarbonate solution followed by washing twice, each time with 250 ml. of cold water. The ethereal solution is dried over anhydrous sodium sulfate and filtered. The solvent is removed in vacuo to obtain ethyl α-chloro-γ-(2'-chloro-4-biphenylyl)butyrate.

EXAMPLE 2

α-Chloro-γ-(2'-chloro-4-biphenylyl)butyric acid

A mixture of 0.167 moles of ethyl α-chloro-γ-(2'-4-biphenylyl)butyrate and 160 ml. of glacial acetic acid containing 40 ml. of 37% hydrochloric acid is refluxed for 20 hours. The mixture is concentrated under reduced pressure to give a gummy residue. The latter material is dissolved in 300 ml. of n-hexane, washed with ice-cold water (100 ml. total), dried over sodium sulfate and filtered. The hexane is removed to give α-chloro-γ-(2'-chloro-4-biphenylyl)butyric acid.

A. In a similar manner the esters of this invention may be converted to the corresponding acids.

EXAMPLE 3

α-Chloro-γ-(2'-chloro-4-biphenylyl)butyric acid, sodium salt

A solution of 12.4 g. of sodium bicarbonate in 135 ml. water is added dropwise to a stirred solution of 0.164 moles of α-chloro-γ-(2'-chloro-4-biphenylyl)-butyric acid in 150 cc. of methanol. The solvent is removed in vacuo and the residue is dried by repeated distillations with anhydrous ethanol. The crystalline residue is triturated with ether (100 cc.), collected on a filter, and washed with ether. Drying in a vacuum desiccator affords α-chloro-γ-(2'-chloro-4-biphenyl)-butyric acid, sodium salt.

A. When an equimolar amount of sodium bicarbonate in the above reaction is replaced by it compounds below, then the corresponding salt is prepared.

| sodium hydroxide | potassium hydroxide |
|---|---|
| calcium hydroxide | potassium carbonate |
| magnesium bicarbonate | |

When the α-chloro alkanoic acid compounds of this invention are used in the above reaction, then the corresponding salts are prepared.

EXAMPLE 4

α-Chloro-γ-(2'-chloro-4-biphenylyl)butyric acid, diethylammonium salt

Anhydrous diethylamine (0.11 moles) is added dropwise to a stirred solution of α-chloro-γ-(2'-chloro-4-biphenylyl)butyric acid (0.10 moles) in 100 ml. of n-hexane at 0°C. The precipitate is collected on a filter, washed with n-hexane, and dried in a vacuum desiccator to obtain α-chloro-γ-(2'-chloro-4-biphenylyl)-butyric acid, diethylammonium salt.

When diethylamine in the above reaction is replaced by an equimolar amount of the compounds below, then the corresponding product is prepared.

| dimethylamine | α-methylbenzylamine |
|---|---|
| β-hydroxyethylamine | cyclohexylamine |
| piperazine | triethylamine |
| piperidine | phenethylamine |

B. When the α-chloro alkanoic acid compounds of this invention are used in the above reaction, then the corresponding salts are prepared.

I claim:
1. α-chloro-γ-(p-i-propylphenyl)butyric acid.
2. α-chloro-γ-(p-i-butylphenyl)butyric acid.

* * * * *